(12) United States Patent
Uchikawa et al.

(10) Patent No.: US 8,246,544 B2
(45) Date of Patent: Aug. 21, 2012

(54) ULTRASONIC DIAGNOSIS APPARATUS

(75) Inventors: Akiko Uchikawa, Tokyo (JP);
Yoshihiko Ito, Tokyo (JP); Yasuhiro Nakamura, Kanagawa (JP)

(73) Assignee: Panasonic Corporation, Osaka (JP)

( * ) Notice: Subject to any disclaimer, the term of this patent is extended or adjusted under 35 U.S.C. 154(b) by 1264 days.

(21) Appl. No.: 10/585,388

(22) PCT Filed: Jan. 6, 2005

(86) PCT No.: PCT/JP2005/000074
§ 371 (c)(1),
(2), (4) Date: Jul. 7, 2006

(87) PCT Pub. No.: WO2005/065547
PCT Pub. Date: Jul. 21, 2005

(65) Prior Publication Data
US 2009/0198138 A1 Aug. 6, 2009

(30) Foreign Application Priority Data
Jan. 8, 2004 (JP) .................................. 2004-003310

(51) Int. Cl.
*A61B 8/00* (2006.01)
(52) U.S. Cl. ........ 600/453; 600/455; 600/457; 600/459; 382/128; 382/154; 73/632; 73/633; 73/642
(58) Field of Classification Search .................. 600/459, 600/453, 455, 457; 382/128, 154, 260–265; 73/602, 620–621, 627, 632–633, 642, 584, 73/587, 596
See application file for complete search history.

(56) References Cited

U.S. PATENT DOCUMENTS

| | | | |
|---|---|---|---|
| 5,318,033 A | 6/1994 | Savord | |
| 5,779,640 A * | 7/1998 | Holley et al. | 600/447 |
| 5,976,087 A | 11/1999 | Resnick et al. | |
| 6,142,942 A | 11/2000 | Clark | |
| 6,283,919 B1 | 9/2001 | Roundhill et al. | |
| 6,679,846 B2 * | 1/2004 | Napolitano et al. | 600/447 |
| 7,604,596 B2 * | 10/2009 | Hwang et al. | 600/443 |
| 2003/0097068 A1 | 5/2003 | Hossack et al. | |

FOREIGN PATENT DOCUMENTS

| | | |
|---|---|---|
| JP | 6-14929 | 1/1994 |
| JP | 7-8492 | 1/1995 |
| JP | 10-118063 | 5/1998 |
| JP | 10-328185 | 12/1998 |
| JP | 2001-340338 | 12/2001 |

OTHER PUBLICATIONS

Copy of Japanese Office Action, dated Dec. 16, 2008.

* cited by examiner

*Primary Examiner* — Brian Casler
*Assistant Examiner* — Daniel Huntley
(74) *Attorney, Agent, or Firm* — Hamre, Schumann, Mueller & Larson, P.C.

(57) ABSTRACT

There is provided a first storage for storing digital reception beam data converted from a reception beam formed from an ultrasonic received signal; a first control component for controlling reading and writing of data from/in the first storage; a filter coefficient calculation portion for calculating a filter coefficient based on information on the reception beam, the information including a positional relationship between the reception beam and a transmission beam; and a first spatial filter operation portion for subjecting each of a plurality of the reception beam data including data of beams received in parallel from a single transmission beam to filtering processing for reducing a difference in image quality between adjacent beams based on the filter coefficient. Image data output from the first spatial filter operation portion are converted into scanning of a display monitor so as to display an image on the display monitor.

6 Claims, 15 Drawing Sheets

ULTRASONIC DIAGNOSIS APPARATUS

TECHNICAL FIELD

The present invention relates to an ultrasonic diagnosis apparatus having a parallel reception function of forming a plurality of reception beams from a single transmission beam.

BACKGROUND ART

As shown in FIG. 13, an ultrasonic diagnosis apparatus obtains two-dimensional information by scanning ultrasonic beams with an ultrasonic probe 30 for transmitting and receiving ultrasonic waves to/from a subject, and displays an ultrasonic image based on the two-dimensional information. A signal received by the ultrasonic probe 30 is supplied to a spatial filter processing circuit 32 through a signal processing portion 31. The spatial filter processing circuit 32, which is provided before an image display conversion portion 33, includes a spatial filter for reducing noise in the received signal. A control circuit 34 controls the spatial filter processing circuit 32 so that a filter coefficient is changed in a direction from the vicinity of a surface of an oscillator toward a distal point in acoustic data. In other words, according to the conventional ultrasonic diagnosis apparatus, in spatial filter processing of the acoustic data before coordinate transformation, the filter coefficient is changed in accordance with a distance on the acoustic line data (see, for example, Patent document 1).

Patent document 1: JP 2001-340338 A (FIG. 1)

DISCLOSURE OF INVENTION

Problem to be Solved by the Invention

In the conventional ultrasonic diagnosis apparatus, a signal difference between a plurality of reception beams that are obtained from a single transmission beam with a parallel reception function is smaller than a signal difference between reception beams obtained from different transmission beams. Therefore, when the filter coefficient for reducing a difference in image quality between adjacent beams is fixed, there arise the following problems. That is, between signals of reception beams obtained from a single transmission beam, the filter works excessively, and thus an image is made uniform due to a smoothing effect and detail of the image cannot be displayed. On the other hand, between signals of reception beams obtained from different transmission beams, the filter hardly works, and thus boundaries between the reception beams are displayed due to the effect of edge reinforcement.

In particular, in two-dimensional Doppler, transmission and reception are repeated about ten times on the same acoustic line so as to detect a temporal variation, and therefore a large amount of time elapses between different transmission beams. Accordingly, there is a significant variation between reception beams obtained from a single transmission beam and reception beams obtained from different transmission beams. This noticeably results in a uniform image or visible boundaries between the reception beams, causing stripes to be generated in a direction in which acoustic lines are arranged. Moreover, in two-dimensional Doppler, when a temporal variation is indicated by coloring, a boundary between a non-colored portion where a temporal variation is zero and a colored portion where a temporal variation occurs is shown clearly, and therefore stripes are generated in the direction of acoustic lines depending upon the presence/absence of data.

The present invention has been made to solve the above-mentioned conventional problems, and its object is to provide an ultrasonic diagnosis apparatus that optimizes filtering processing with respect to signals between a plurality of reception beams obtained from a single transmission beam, thereby displaying a high-quality ultrasonic image in which stripes are generated less in a direction in which acoustic lines are arranged and that is well defined in detail.

Means for Solving Problem

In order to achieve the above-mentioned object, an ultrasonic diagnosis apparatus according to the present invention includes: first storage means (memory) for storing digital reception beam data converted from a reception beam formed from an ultrasonic received signal; first control means (memory control portion, first memory control portion) for controlling reading and writing of data from/in the first storage means; a filter coefficient calculation portion for calculating a filter coefficient based on information on the reception beam, the information including a positional relationship between the reception beam and a transmission beam; and a first spatial filter operation portion for subjecting each of a plurality of the reception beam data including data of beams received in parallel from a single transmission beam to filtering processing for reducing a difference in image quality between adjacent beams based on the filter coefficient, wherein image data output from the first spatial filter operation portion are converted into scanning of a display monitor so as to display an image on the display monitor.

With this configuration, the filter coefficients can be controlled optimally with respect to signals between a plurality of the reception beams including ones received in parallel from a single transmission beam, in accordance with a position of each of the reception beams with respect to a transmission beam. As a result, it becomes possible to display a high-quality ultrasonic image in which stripes are generated less in a direction in which acoustic lines are arranged and that is well defined in detail.

The ultrasonic diagnosis apparatus with the above configuration further can include: a two-dimensional Doppler signal processing portion for subjecting reception beam data from an ultrasonic reception data processing portion to two-dimensional Doppler processing; second storage means (two-dimensional Doppler memory) for storing two-dimensional Doppler data output from the two-dimensional Doppler signal processing portion; second control means (second memory control portion) for controlling reading and writing of data from/in the second storage means; and a second spatial filter operation portion for subjecting each of a plurality of the received two-dimensional Doppler data including data of beams received in parallel from a single transmission beam to filtering processing for reducing a difference in image quality between adjacent beams based on the filter coefficient supplied from the filter coefficient calculation portion.

With this configuration, in the ultrasonic diagnosis apparatus having the two-dimensional Doppler function, the filter coefficients can be controlled optimally with respect to signals between a plurality of the reception beams including ones received in parallel from a single transmission beam, in accordance with a position of each of the reception beams with respect to a transmission beam. As a result, it becomes possible to display a high-quality ultrasonic image that is well defined in detail with reduced noticeable stripes seen in two-dimensional Doppler in a direction in which acoustic lines are arranged.

In the ultrasonic diagnosis apparatus with the above configuration, it is possible that the filter coefficient calculation portion is able to control the filter coefficient in accordance with a receiving depth.

With this configuration, in the case where a distance between acoustic lines is different depending upon the depth, filter coefficients of stronger correlation can be set for a shallow portion, and filter coefficients of weaker correlation can be set for a deep portion. As a result, it is possible to display a high-quality ultrasonic image with little lateral shift.

In the ultrasonic diagnosis apparatus with the above configuration, it is possible that the filter coefficient calculation portion is able to control the filter coefficient in accordance with an angle of the reception beam.

With this configuration, in the case where transmission and reception are performed with angled acoustic lines, the filter coefficients can be optimized such that, for example, filter coefficients of weak correlation are set between the same depths. As a result, it is possible to display a high-quality ultrasonic image with little lateral shift. Further, in the case where a deflection angle is different depending upon the acoustic line, the optimization of the filter coefficients allows beam distortion to be corrected.

In the ultrasonic diagnosis apparatus with the above configuration, it is possible that the filter coefficient calculation portion is able to control the filter coefficient in accordance with a focal position of the transmission beam.

With this configuration, the filter coefficients can be optimized such that, for example, filter coefficients of weak correlation are set for the vicinity of the focal position of the transmission beam, and filter coefficients of strong correlation are set for positions away from the focal position of the transmission beam. As a result, it is possible to display a high-quality ultrasonic image that is uniform regardless of the focal position of the transmission beam.

Effects of the Invention

According to the present invention, it is possible to achieve a particular effect of providing an ultrasonic diagnosis apparatus that optimizes filtering processing with respect to signals between a plurality of reception beams obtained from a single transmission beam, thereby displaying a high-quality ultrasonic image in which stripes are generated less in a direction in which acoustic lines are arranged and that is well defined in detail.

EXPLANATION OF LETTERS OR NUMERALS

Figure 1:
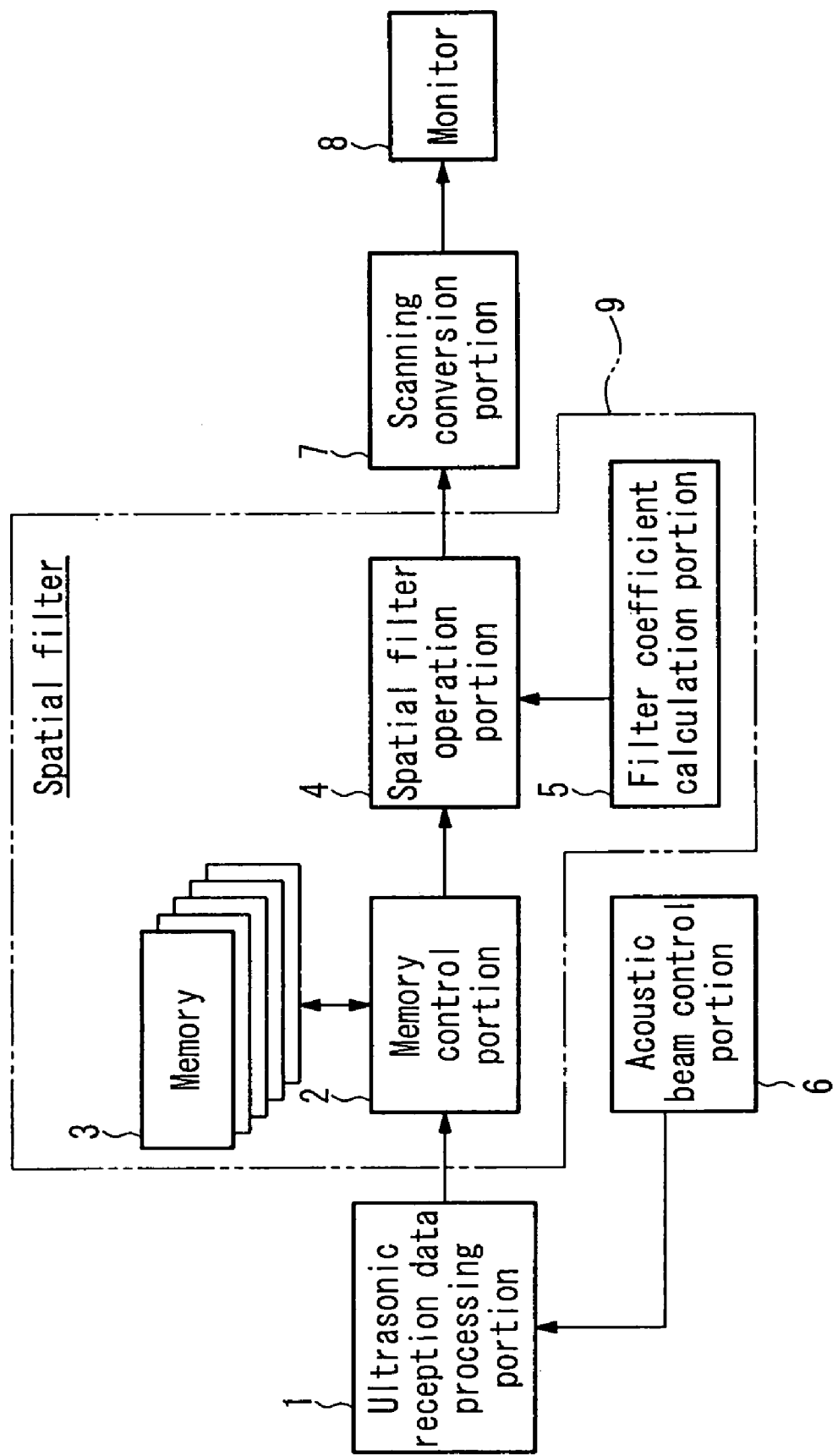
FIG. 1 is a functional block diagram showing an exemplary configuration of an ultrasonic diagnosis apparatus according to a first embodiment of the present invention.

1 Ultrasonic reception data processing portion
2 Memory first storage means)
3 Memory control portion, first memory control portion (first control means)
4 Spatial filter operation portion, first spatial filter operation portion
5, 16, 19, 23 Filter coefficient calculation portion
6 Acoustic beam control portion
7 Scanning conversion portion
8 Monitor (display means)
9, 15, 16 Spatial filter
10 Brightness signal processing portion
11 Two-dimensional Doppler signal processing portion
12 Two-dimensional Doppler memory (second storage means)
13 Second memory control portion (second control means)

14 Second spatial filter operation portion
17 Depth information generation portion
18, 21, 22 Acoustic line
20 Beam angle information generation portion
24 Transmission beam focal position information generation portion

DESCRIPTION OF THE INVENTION

Hereinafter, preferred embodiments of the present invention will be described in detail with reference to the drawings.

First Embodiment

FIG. 1 is a functional block diagram showing an exemplary configuration of an ultrasonic diagnosis apparatus according to a first embodiment of the present invention.

This ultrasonic diagnosis apparatus includes an ultrasonic reception data processing portion 1 for forming a reception beam of an ultrasonic received signal and converting the reception beam into digital reception beam data, a spatial filter 9, an acoustic beam control portion 6 for supplying information on the reception beam to the ultrasonic reception data processing portion 1, a scanning conversion portion 7 for converting output data from the spatial filter 9 into image data, and a monitor 8 (display means) for displaying the image data.

The spatial filter 9 includes memories 3 (first storage means) for storing the reception beam data supplied from the ultrasonic reception data processing portion 1, a memory control portion 2 (first control means) for controlling reading and writing of data from/in the memories 3, a spatial filter operation portion 4 (first spatial filter operation portion) for subjecting data read by the memory control portion 2 to filtering processing, and a filter coefficient calculation portion 5 for calculating a filter coefficient and supplying the same to the spatial filter operation portion 4.

The filter coefficient calculation portion 5 calculates the filter coefficient based on the information on the reception beam, the information including a positional relationship between the reception beam and a transmission beam. The positional relationship between the reception beam and a transmission beam is, for example, information on whether or not the reception beams are formed from a single transmission beam. The spatial filter operation portion 4 subjects a plurality of the reception beam data to filtering processing for reducing a difference in image quality between adjacent beams, based on the filter coefficients supplied from the filter coefficient calculation portion 5, and supplies the resultant output data to the scanning conversion portion 7. The information on the reception beam may be supplied directly to the memory control portion 2 and the filter coefficient calculation portion 5.

Next, an operation of the ultrasonic diagnosis apparatus thus configured will be described with reference to FIGS. 2A, 2B, 3A, 3B, 4A to 4C, and 5A to 5C. In particular, a description will be given mainly of the spatial filter 9 as a principal component of the present invention.

In the present embodiment, when a plurality of reception beams are formed from a single transmission beam, the filter coefficients are not set in a bilaterally symmetrical manner but are set to values that allow a difference in correlation between image data to be canceled. More specifically, image data on a plurality of reception beams formed from a single transmission beam are multiplied by small filter coefficients, since such image data show a strong correlation with each other. On the other hand, image data on reception beams formed from different reception beams are multiplied by large filter coefficients. By setting the filter coefficients in this manner, a possible difference in image quality between adjacent beams is reduced. The following description is directed to such filtering processing.

Figure 2A:
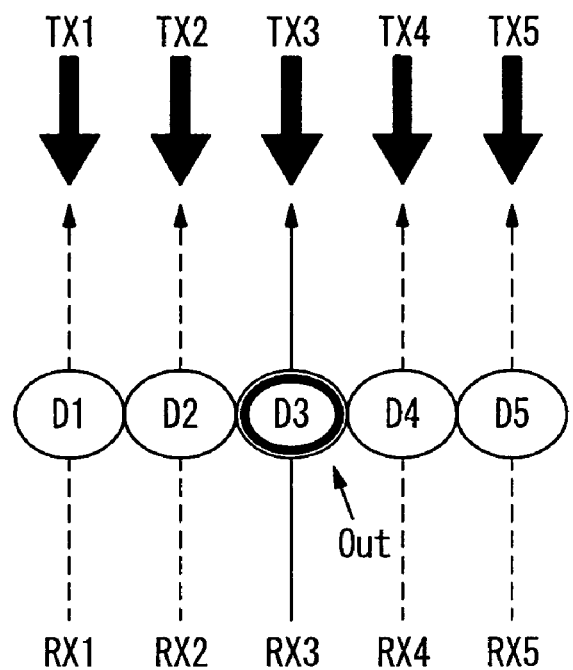
FIG. 2A is a schematic diagram showing image data at an arbitrary depth in the case where each single reception beam is formed from a single transmission beam and where a lateral filter is used in the first embodiment.
Figure 2B:
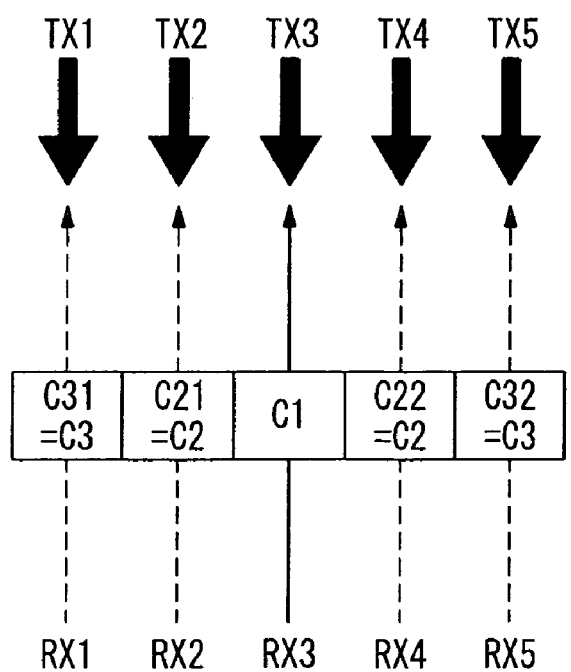
FIG. 2B is a schematic diagram showing filter coefficients corresponding to the image data in FIG. 2A.

First, with reference to FIGS. 2A and 2B, a description will be given of the filtering processing for reducing a difference in image quality between adjacent beams in the case where each single reception beam is formed from a single transmission beam and where, for example, a lateral filter is used. This processing is carried out in the same manner as in the prior art. FIG. 2A is a schematic diagram showing image data at an arbitrary depth in the case of using a lateral filter. FIG. 2B is a schematic diagram showing the filter coefficients corresponding to the image data in FIG. 2A.

FIGS. 2A and 2B show a state where reception beams RX1, RX2, RX3, RX4, and RX5 are formed from transmission beams TX1, TX2, TX3, TX4, and TX5, respectively. In FIGS. 2A, D1, D2, D3, D4, and D5 represent image data on the reception beams RX1, RX2, RX3, RX4, and RX5, respectively, at an arbitrary depth. Herein, the description is directed to the case where, for example, the lateral filter forms a single beam from the five reception beams. As shown in FIG. 2B, it is assumed that the filter coefficient for forming data at an arbitrary sampling point on the reception beam RX3 is C1. Similarly, it is assumed that the filter coefficient corresponding to the reception beam RX2 is C21, the filter coefficient corresponding to the reception beam RX4 is C22, the filter coefficient corresponding to the reception beam RX1 is C31, and the filter coefficient corresponding to the reception beam RX5 is C32. In this case, output data "Out" obtained as a result of the filtering are expressed by the following Formulas (1) and (2).

$$\text{Out} = (D1 \times C31 + D2 \times C21 + D3 \times C1 + D4 \times C22 + D5 \times C32) \quad \text{Formula (1)}$$

$$C31 + C21 + C1 + C22 + C32 = 1 \quad \text{Formula (2)}$$

In general, as shown in FIG. 2B, the filter coefficients in the filtering processing for reducing a difference in image quality between adjacent beams are set such that the filter coefficient C1 for the same position as that of the arbitrary sampling point (Out) is set to a maximum value and the other filter coefficients are set in a bilaterally symmetrical manner with respect to C1. That is to say, the filter coefficients C21, C22, C31, and C32 are expressed by the following Formula (3).

$$C21 = C22 = C2, C31 = C32 = C3 \quad \text{Formula (3)}$$

When the filter coefficients assume positive values, the output data "Out" obtained as a result of the filtering are expressed by the following Formulas (4), (5), and (6).

$$\text{Out} = (D1 \times C3 + D2 \times C2 + D3 \times C1 + D4 \times C2 + D5 \times C3) \quad \text{Formula (4)}$$

$$C3 + C2 + C1 + C2 + C3 = 1 \quad \text{Formula (5)}$$

$$C1 > C2 > C3 \quad \text{Formula (6)}$$

Figure 3A:
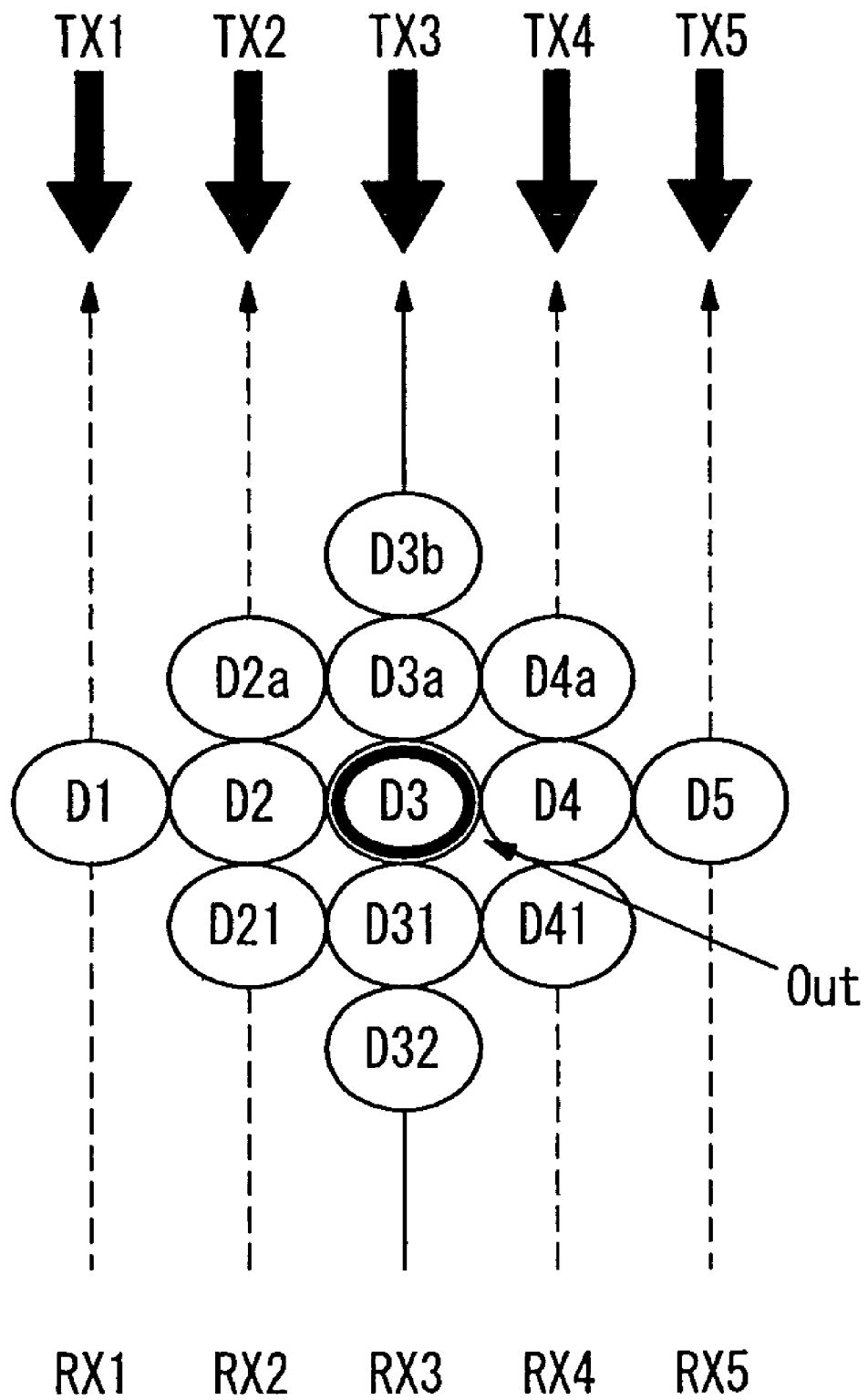
FIG. 3A is a schematic diagram showing image data at an arbitrary depth in the case where each single reception beam is formed from a single transmission beam and where a diamond-shaped filter is used in the first embodiment.
Figure 3B:
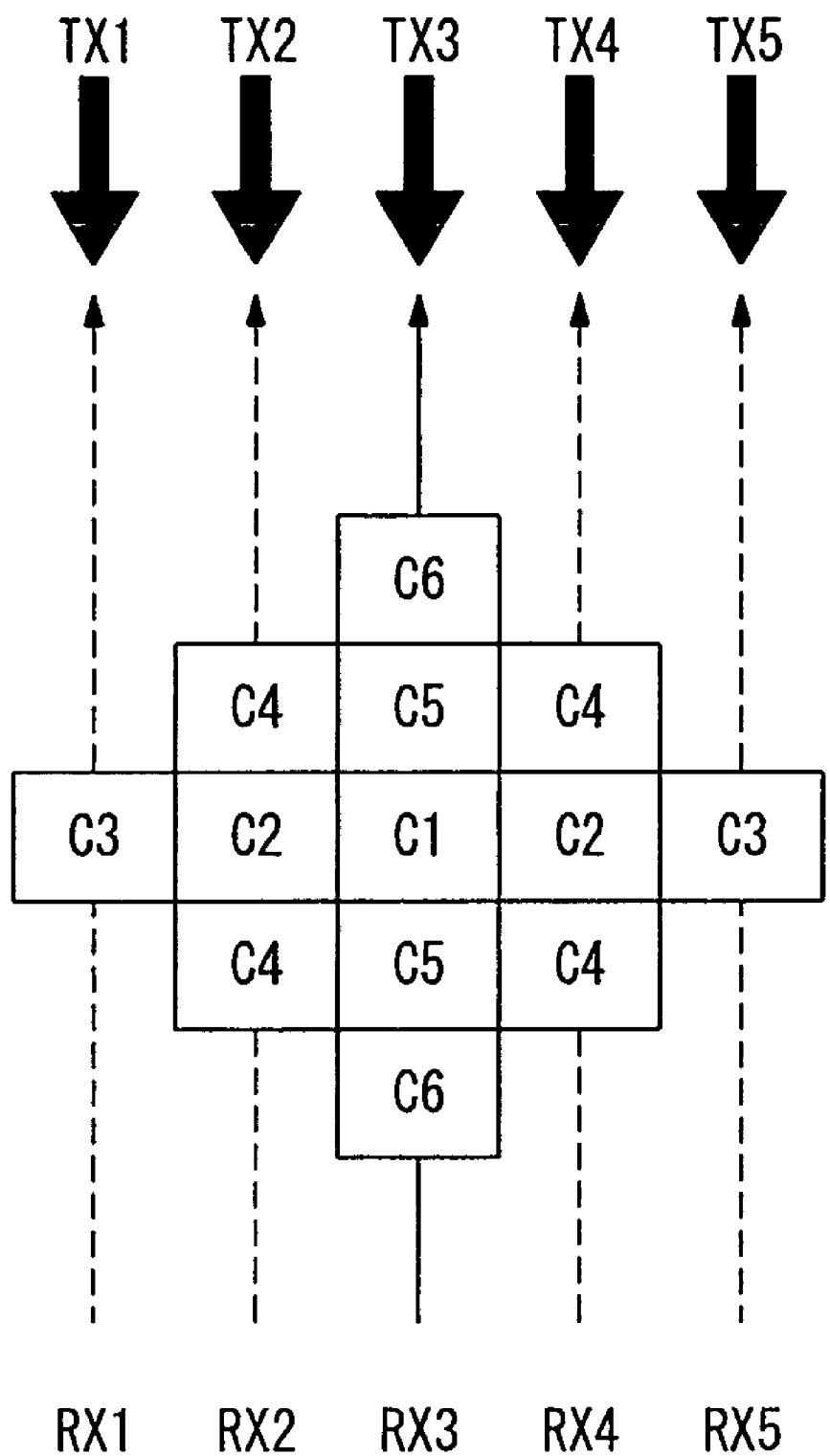
FIG. 3B is a schematic diagram showing filter coefficients corresponding to the image data in FIG. 3A.

FIGS. 3A and 3B show the setting of the filter coefficients in the case where a diamond-shaped filter is used instead of a lateral filter. FIGS. 3A and 3B are a schematic diagram showing image data at an arbitrary depth, and a schematic diagram showing the filter coefficients corresponding thereto, respectively, in the case of using a diamond-shaped filter.

Also in the case of using a diamond-shaped filter, the filter coefficients are set as in the case of using a lateral filter such that a filter coefficient C1 for the same position as that of an arbitrary sampling point (Out) is set to a maximum value and the other filter coefficients are set in a bilaterally and vertically symmetrical manner with respect to the filter coefficient C1. Herein, it is assumed that data at an arbitrary sampling point on a reception beam RX3 are formed, and when the filter coefficients assume positive values, output data "Out" obtained as a result of the filtering are expressed by the following Formulas (7), (8), and (9).

$$\begin{aligned}\text{Out} = \\ (D1 \times C3 + D2 \times C2 + D3 \times C1 + D4 \times C2 + D5 \times C3) + \\ (D2a \times C4 + D3a \times C5 + D4a \times C4) + \\ (D21 \times C4 + D31 \times C5 + D41 \times C4) + \\ D3b \times C6 + D32 \times C6\end{aligned} \quad \text{Formula (7)}$$

$$C1 + 2 \times C2 + 2 \times C3 + 4 \times C4 + 2 \times C5 + 2 \times C6 = 1 \quad \text{Formula (8)}$$

$$C1 > C2 > C3,\ C1 > C5 > C6,\ C5 > C4,\ \text{and } C2 > C4 \quad \text{Formula (9)}$$

Next, with reference to FIGS. 4A to 4C, a description will be given of the filtering processing for reducing a difference in image quality between adjacent beams in the case where a plurality of reception beams are formed from a single transmission beam and where, for example, a lateral filter is used for forming two reception beams. This processing is carried out on the condition characteristic of the present embodiment.

Figure 4A:
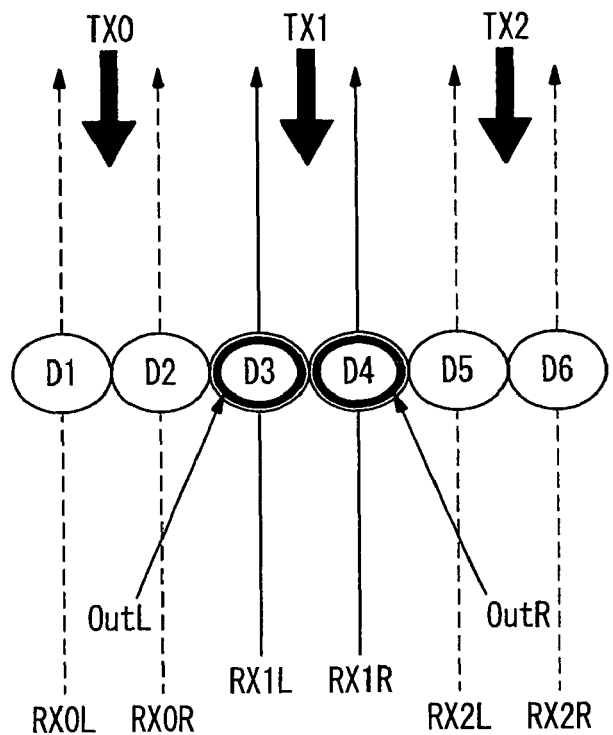
FIG. 4A is a schematic diagram showing image data at an arbitrary depth in the case where two reception beams are formed from a single transmission beam and where a lateral filter is used in the first embodiment.

FIG. 4A is a schematic diagram showing image data at an arbitrary depth. FIGS. 4B and 4C are schematic diagrams showing the filter coefficients for forming data "OutL" at an arbitrary sampling point on a reception beam RX1L, and the filter coefficients for forming data "OutR" at an arbitrary sampling point on a reception beam RX1R, respectively, in the case of using a lateral filter.

Figure 4B:
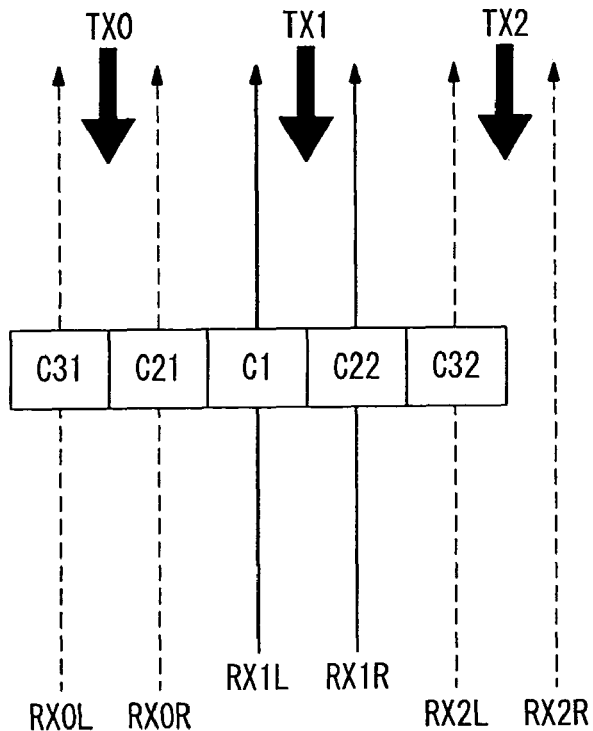
FIG. 4B is a schematic diagram showing filter coefficients for forming data "OutL" at an arbitrary sampling point on a reception beam RX1L from the image data in FIG. 4A.
Figure 4C:
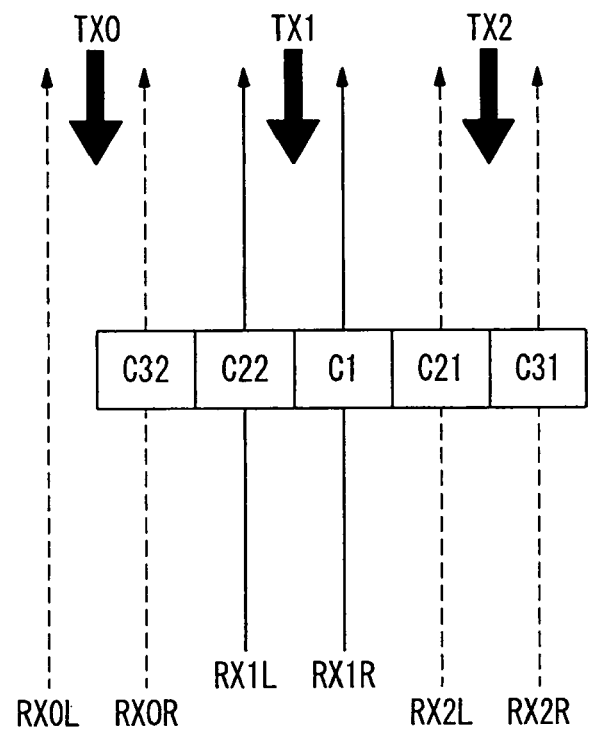
FIG. 4C is a schematic diagram showing filter coefficients for forming data "OutR" at an arbitrary sampling point on a reception beam RX1R from the image data in FIG. 4A.

As shown in FIGS. 4A to 4C, two reception beams RX0L and RX0R, two reception beams RX1L and RX1R, and two reception beams RX2L and RX2R are formed from a transmission beam TX0, a transmission beam TX1, and a transmission beam TX2, respectively.

In FIGS. 4A, D1, D2, D3, D4, D5, and D6 represent image data on the reception beams RX0L, RX0R, RX1L, RX1R, RX2L, and RX2R, respectively, at an arbitrary depth. Since the image data D1 and D2 are obtained from the same transmission beam TX0, these data show a strong correlation with each other, and in many cases their values are closer to each other than values of D2 and D3. Such a relationship is expressed by the following Formula (10). Similarly, there is also a strong correlation between D3 and D4 and between D5 and D6.

$$|D1-D2|<|D3-D2| \quad \text{Formula (10)}$$

It is assumed that a single beam is formed from five beams and that the filter coefficients for forming data "OutL" at an arbitrary sampling point on the reception beam RX1L are C1, C21, C22, C31, and C32 as shown in FIG. 4B. In this case, output data "OutL" obtained as a result of the filtering are expressed by the following Formulas (11) and (12).

$$\text{Out}L=(D1 \times C31+D2 \times C21+D3 \times C1+D4 \times C22+D5 \times C32) \quad \text{Formula (11)}$$

$$C31+C21+C1+C22+C32=C1 \quad \text{Formula (12)}$$

Note here that the filter coefficients are not set in a bilaterally symmetrical manner but are set in an asymmetrical manner so as to cancel a difference in correlation between image data obtained from a single transmission beam and image data obtained from different transmission beams as mentioned above. For example, when the filter coefficients assume positive values, they are set so as to satisfy the relationship expressed by the following Formula (13).

$$C22<C21 \quad \text{Formula (13)}$$

By setting the filter coefficients in this manner, the filtering processing for reducing a difference in image quality between adjacent beams is optimized. As a result, it is possible to display a high-quality ultrasonic image in which stripes are generated less in a direction in which acoustic lines are arranged.

Similarly, as shown in FIG. 4C, it is assumed that the filter coefficients for forming data "OutR" at an arbitrary sampling point on the reception beam RX1R are C1, C21, C22, C31, and C32, and when these filter coefficients assume positive values, output data "OutR" obtained as a result of the filtering are expressed by the following Formulas (14), (15), and (16).

$$\text{Out}R=(D2 \times C32+D3 \times C22+D4 \times C1+D5 \times C21+D6 \times C31) \quad \text{Formula (14)}$$

$$C32+C22+C1+C21+C31=1 \quad \text{Formula (15)}$$

$$C22<C21 \quad \text{Formula (16)}$$

Figure 5A:
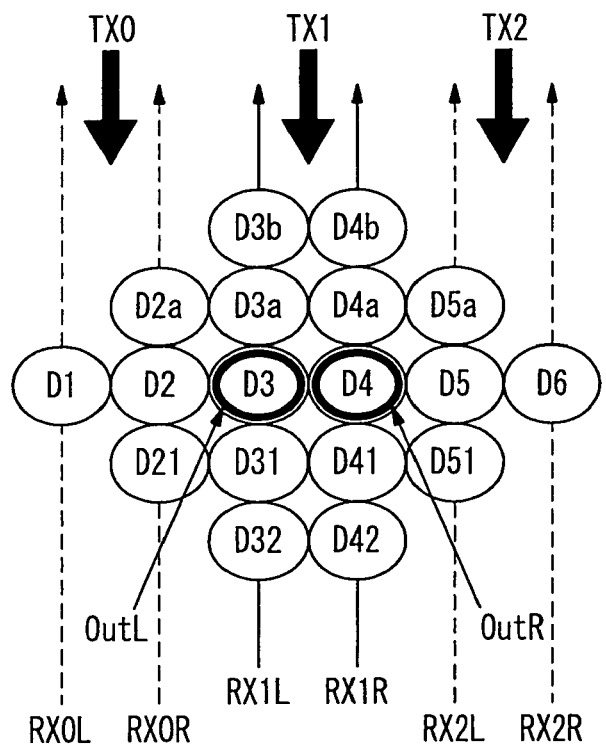
FIG. 5A is a schematic diagram showing image data at an arbitrary depth in the case where two reception beams are formed from a single transmission beam and where a diamond-shaped filter is used in the first embodiment.
Figure 5B:
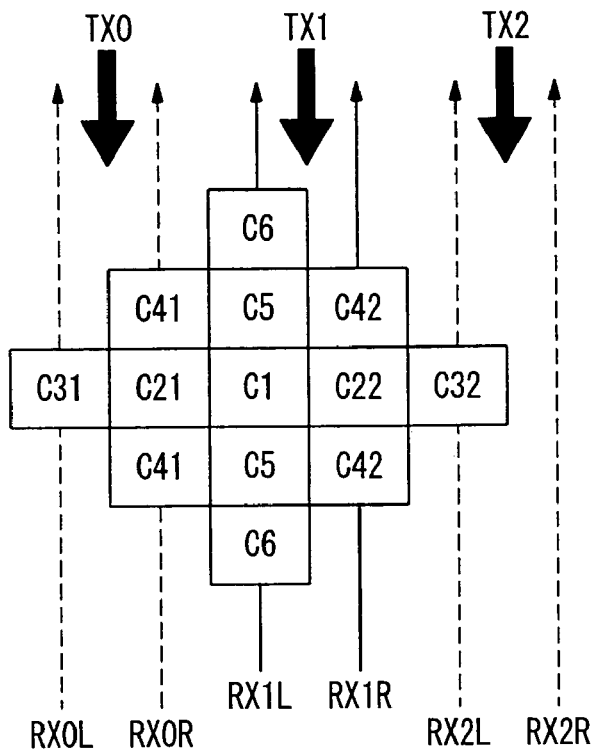
FIG. 5B is a schematic diagram showing filter coefficients for forming data "OutL" at an arbitrary sampling point on a reception beam RX1L from the image data in FIG. 5A.
Figure 5C:
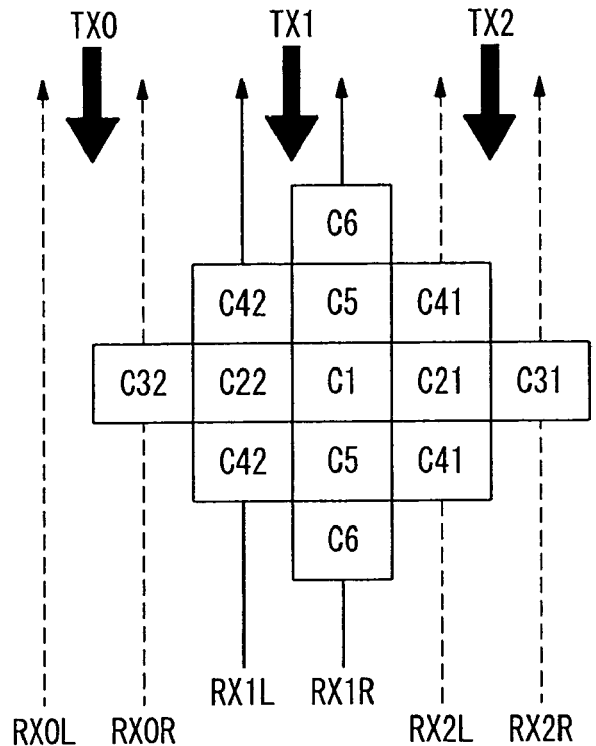
FIG. 5C is a schematic diagram showing filter coefficients for forming data "OutR" at an arbitrary sampling point on a reception beam RX1R from the image data in FIG. 5A.

FIGS. 5A, 5B, and 5C show the setting of the filter coefficients in the case where a diamond-shaped filter is used instead of a lateral filter. FIG. 5A is a schematic diagram showing image data at an arbitrary depth. FIGS. 5B and 5C are schematic diagrams showing the filter coefficients for forming data at an arbitrary sampling point on a reception beam RX1L, and the filter coefficients for forming data at an arbitrary sampling point on a reception beam RX1R, respectively.

Also in the case of using a diamond-shaped filter, the filter coefficients are set as in the case of using a lateral filter in a bilaterally and vertically asymmetrical manner with respect to an arbitrary sampling point (OutL or OutR) so as to cancel a difference in correlation between image data obtained from a single transmission beam and image data obtained from different transmission beams. For example, when the filter coefficients assume positive values, output data "OutL" and output data "OutR" obtained as a result of the filtering are expressed by the following Formulas (17), (18), (19), and (20) using the filter coefficients shown in FIGS. 5B and 5C, respectively.

$$\begin{aligned}\text{Out}L = (D1 \times C31 + D2 \times C21 + \\ D3 \times C1 + D4 \times C22 + D5 \times C32) + \\ (D2a \times C41 + D3a \times C5 + D4a \times C42) + \\ (D21 \times C41 + D31 \times C5 + D41 \times C42) + \\ D3b \times C6 + D32 \times C6\end{aligned} \quad \text{Formula (17)}$$

$$\begin{aligned}\text{Out}R = (D2 \times C32 + D3 \times C22 + \\ D4 \times C1 + D5 \times C21 + D6 \times C31) + \\ (D3a \times C42 + D4a \times C5 + D5a \times C41) + \\ (D31 \times C42 + D41 \times C5 + D51 \times C41) + \\ D4b \times C6 + D42 \times C6\end{aligned} \quad \text{Formula (18)}$$

$$C1 + C21 + C22 + C31 + C32 + \\ 2 \times C41 + 2 \times C42 + 2 \times C5 + 2 \times C6 = 1 \quad \text{Formula (19)}$$

$$C21 > C22 \text{ and } C41 > C42 \quad \text{Formula (20)}$$

As described above, according to the present embodiment, the filter coefficients can be controlled optimally with respect to signals between a plurality of reception beams including ones received in parallel from a single transmission beam, in accordance with a position of each of the reception beams with respect to a transmission beam. As a result, it becomes possible to display a high-quality ultrasonic image in which stripes are generated less in a direction in which acoustic lines are arranged and that is well defined in detail. Further, the optimization of the filter coefficients allows, beam distortion to be corrected.

Second Embodiment

Figure 6:
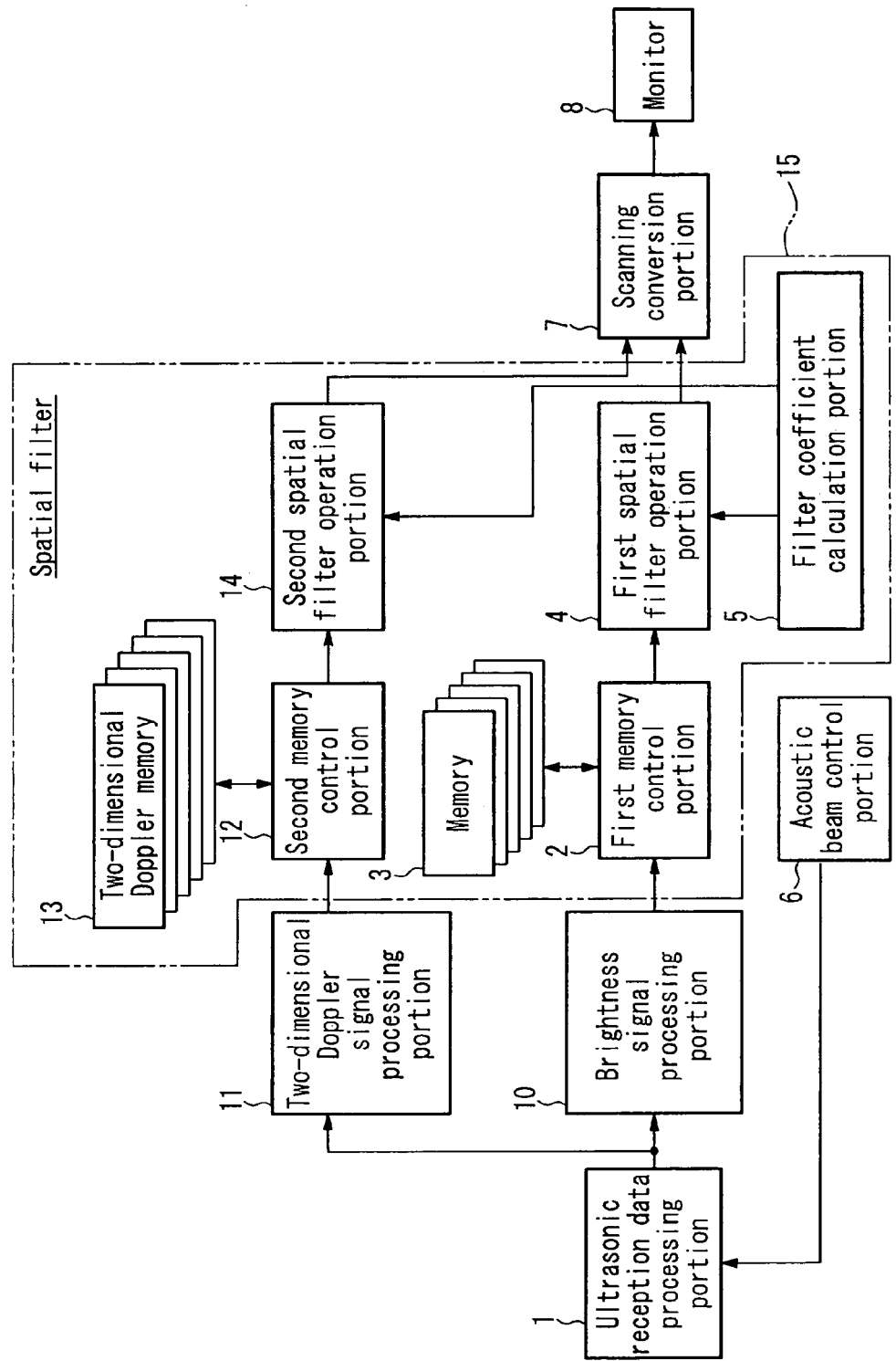
FIG. 6 is a functional block diagram showing an exemplary configuration of an ultrasonic diagnosis apparatus according to a second embodiment of the present invention.

FIG. 6 is a functional block diagram showing an exemplary configuration of an ultrasonic diagnosis apparatus according to a second embodiment of the present invention. The present embodiment is directed to an ultrasonic diagnosis apparatus having a two-dimensional Doppler (color Doppler) function. This ultrasonic diagnosis apparatus has the same configuration as that in the first embodiment except for additional components for achieving the two-dimensional Doppler function. In the following description, the memory control portion 2 and the spatial filter operation portion 4 in FIG. 1 are referred to as a first memory control portion 2 and a first spatial filter operation portion 4, respectively.

The additional components in the present embodiment will be described below. A brightness signal processing portion 10 and a two-dimensional Doppler processing portion 11 are provided between an ultrasonic reception data processing portion 1 and a spatial filter 15. The spatial filter 15 includes the first memory control portion 2, memories 3, the first spatial filter operation portion 4, and a filter coefficient calculation portion 5 as the spatial filter 9 does in the first embodiment, and further includes two-dimensional Doppler memories 13 (second storage means), a second memory control portion 12 (second control means), and a second spatial filter operation portion 14.

Data supplied via the brightness signal processing portion 10 are subjected to the same processing as that in the first embodiment by the first memory control portion 2, the memories 3, and the first spatial filter operation portion 4, and are supplied to a scanning conversion portion 7.

The two-dimensional Doppler signal processing portion 11 subjects reception beam data from the ultrasonic reception data processing portion 1 to two-dimensional Doppler processing. The two-dimensional Doppler memories 13 store the two-dimensional Doppler data output from the two-dimensional Doppler signal processing portion 11. The second memory control portion 12 controls reading and writing of data from/in the two-dimensional Doppler memories 13. The second spatial filter operation portion 14 subjects the received two-dimensional Doppler data read by the second memory control portion 12 to filtering processing in accordance with filter coefficients from the filter coefficient calculation portion 5, and supplies the resultant output data to the scanning conversion portion 7. The filtering processing is carried out with respect to a plurality of the received two-dimensional Doppler data so as to reduce a difference in image quality between adjacent beams.

With this configuration, the ultrasonic diagnosis apparatus having the two-dimensional Doppler (color Doppler) function can control the filter coefficients optimally with respect to signals between a plurality of reception beams including ones received in parallel from a single transmission beam, in accordance with a position of each of the reception beams with respect to a transmission beam. As a result, it becomes possible to display a high-quality ultrasonic image that is well defined in detail with reduced noticeable stripes seen in two-dimensional Doppler in a direction in which acoustic lines are arranged. Further, the optimization of the filter coefficients allows beam distortion to be corrected.

Third Embodiment

Figure 7:
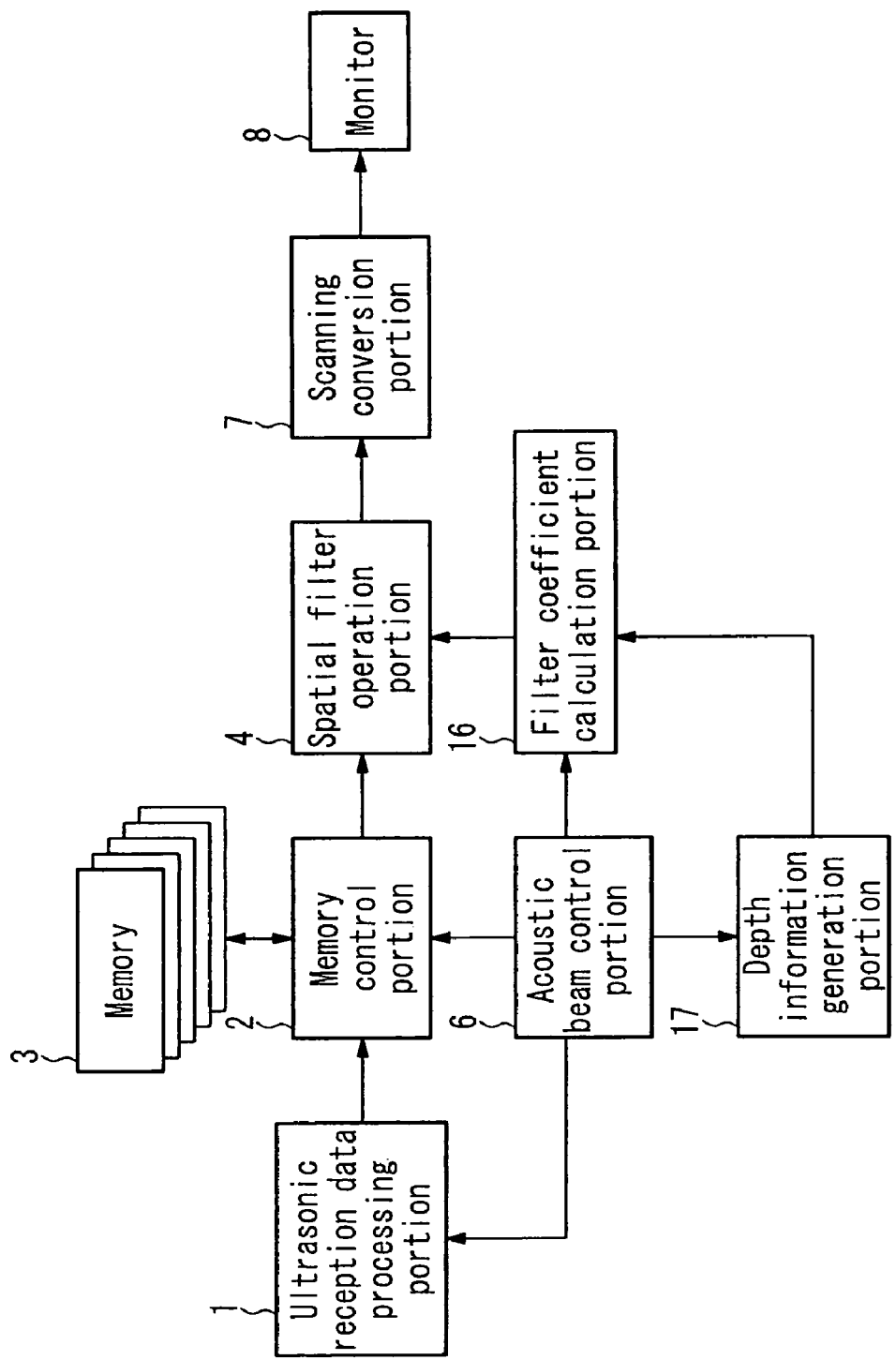
FIG. 7 is a functional block diagram showing an exemplary configuration of an ultrasonic diagnosis apparatus according to a third embodiment of the present invention.

FIG. 7 is a functional block diagram showing an exemplary configuration of an ultrasonic diagnosis apparatus according to a third embodiment of the present invention. The present embodiment is directed to an ultrasonic diagnosis apparatus having a function of controlling filter coefficients in accordance with a receiving depth. This ultrasonic diagnosis apparatus has the same configuration as that in the first embodiment except for an additional component of a depth information generation portion 17 for supplying information on the receiving depth to a filter coefficient calculation portion 16.

Figure 8:
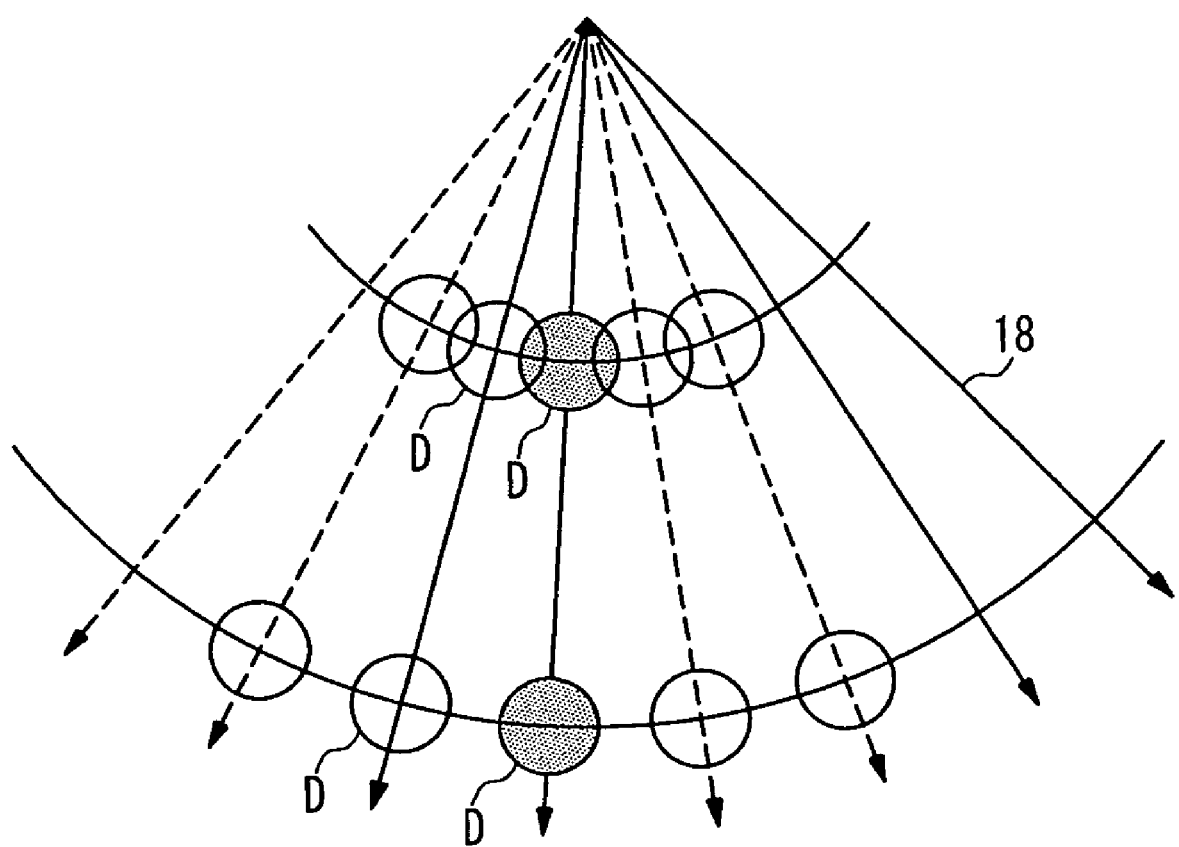
FIG. 8 is a schematic diagram for explaining a function of controlling filter coefficients in the case where a distance between acoustic lines is different depending upon the depth in the third embodiment.

With this configuration, it is possible to set a different filter coefficient depending upon the depth of image data. For example, as shown in FIG. 8, in the case where a distance between acoustic lines 18 is different depending upon the depth, and accordingly a distance between image data D on adjacent acoustic lines 18 is different depending upon the depth, it is possible to reduce a difference in correlation depending upon the depth. In order to reduce such a difference in correlation, filter coefficients of stronger correlation are set for a shallow portion, and filter coefficients of weaker correlation are set for a deep portion. As a result, it is possible to display a high-quality ultrasonic image with little lateral shift.

Fourth Embodiment

Figure 9:
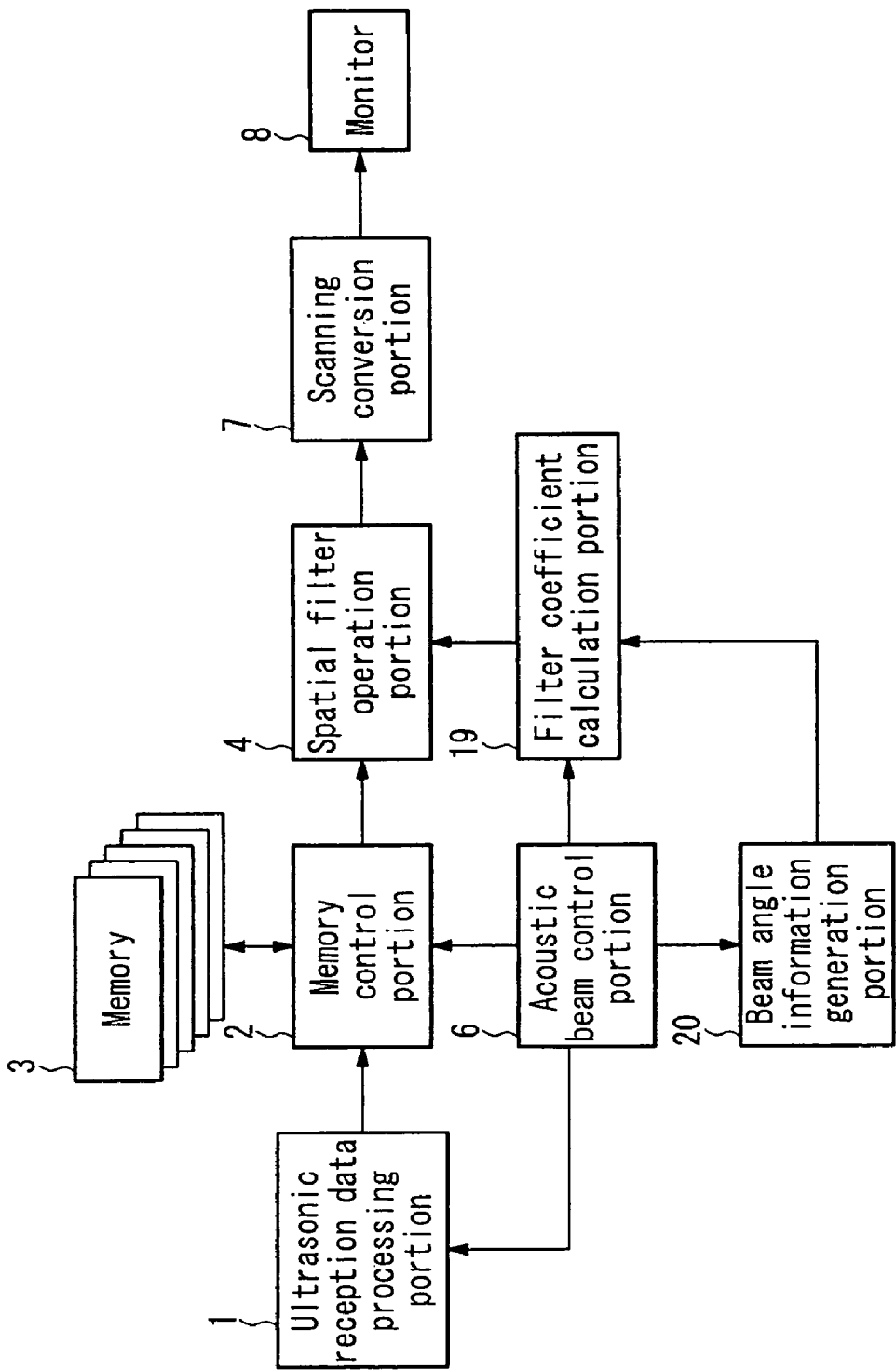
FIG. 9 is a functional block diagram showing an exemplary configuration of an ultrasonic diagnosis apparatus according to a fourth embodiment of the present invention.

FIG. 9 is a functional block diagram showing an exemplary configuration of an ultrasonic diagnosis apparatus according to a fourth embodiment of the present invention. The present embodiment is directed to an ultrasonic diagnosis apparatus having a function of controlling filter coefficients in accordance with an angle of a reception beam. This ultrasonic diagnosis apparatus has the same configuration as that in the first embodiment except for an additional component of a beam angle information generation portion 20 for supplying information on the angle of a reception beam to a filter coefficient calculation portion 19.

Figure 10A:
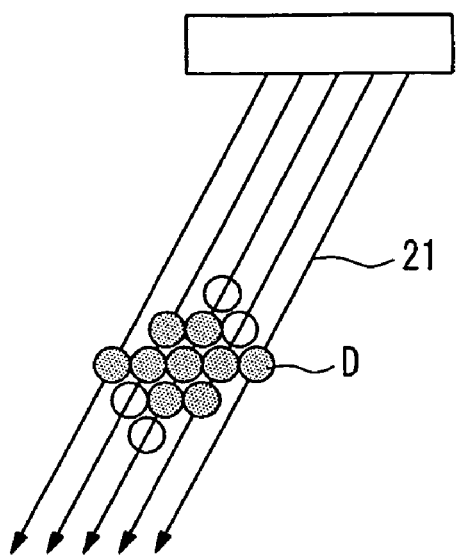
FIG. 10A is a schematic diagram for explaining a function of controlling filter coefficients in the case where transmission and reception are performed with angled acoustic lines in the fourth embodiment.
Figure 10B:
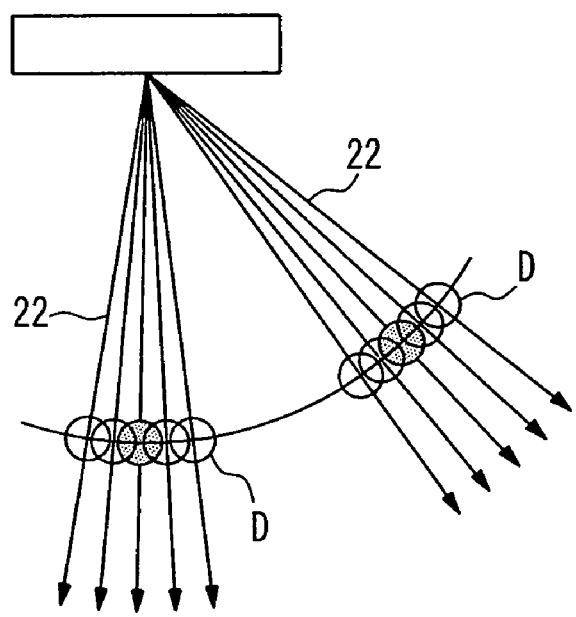
FIG. 10B is a schematic diagram for explaining a function of controlling filter coefficients in the case where a deflection angle is different depending upon the acoustic line in the fourth embodiment.

With this configuration, it is possible to set a different filter coefficient depending upon the angle of a reception beam. For example, as shown in FIG. 10A, in the case where transmission and reception are performed with angled acoustic lines 21, filter coefficients are optimized such that, for example, filter coefficients of weak correlation are set between the same depths. As a result, it is possible to display a high-quality ultrasonic image with little lateral shift. Further, as shown in FIG. 10B, in the case where a deflection angle is different depending upon an acoustic line 22, the optimization of the filter coefficients allows beam distortion to be corrected.

Fifth Embodiment

Figure 11:
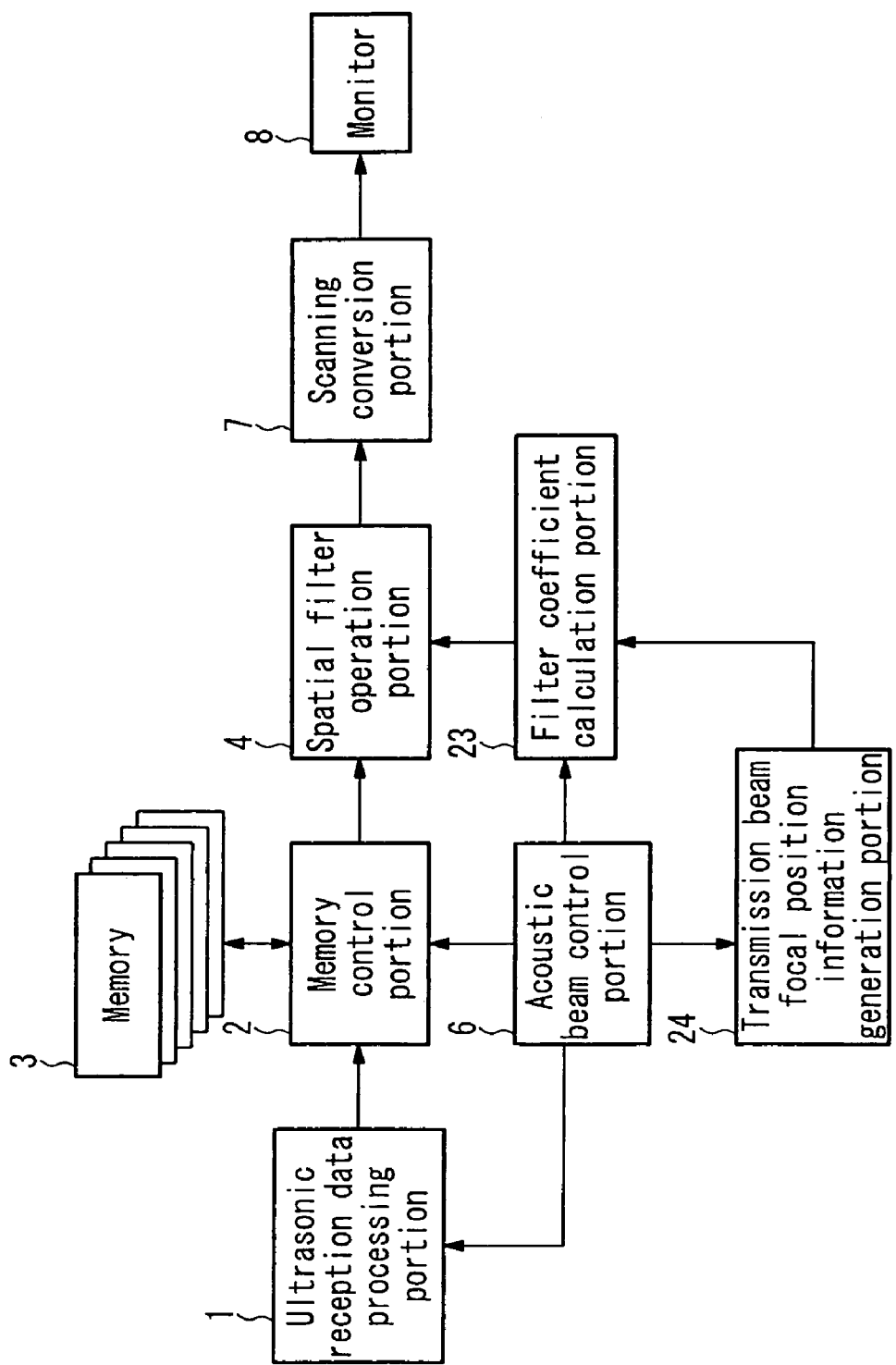
FIG. 11 is a functional block diagram showing an exemplary configuration of an ultrasonic diagnosis apparatus according to a fifth embodiment of the present invention.

FIG. 11 is a functional block diagram showing an exemplary configuration of an ultrasonic diagnosis apparatus according to a fifth embodiment of the present invention. The present embodiment is directed to an ultrasonic diagnosis apparatus having a function of controlling filter coefficients in accordance with a focal position of a transmission beam. This ultrasonic diagnosis apparatus has the same configuration as that in the first embodiment except for an additional component of a transmission beam focal position information generation portion 24 for supplying information on the focal position of a transmission beam to a filter coefficient calculation portion 23.

Figure 12:
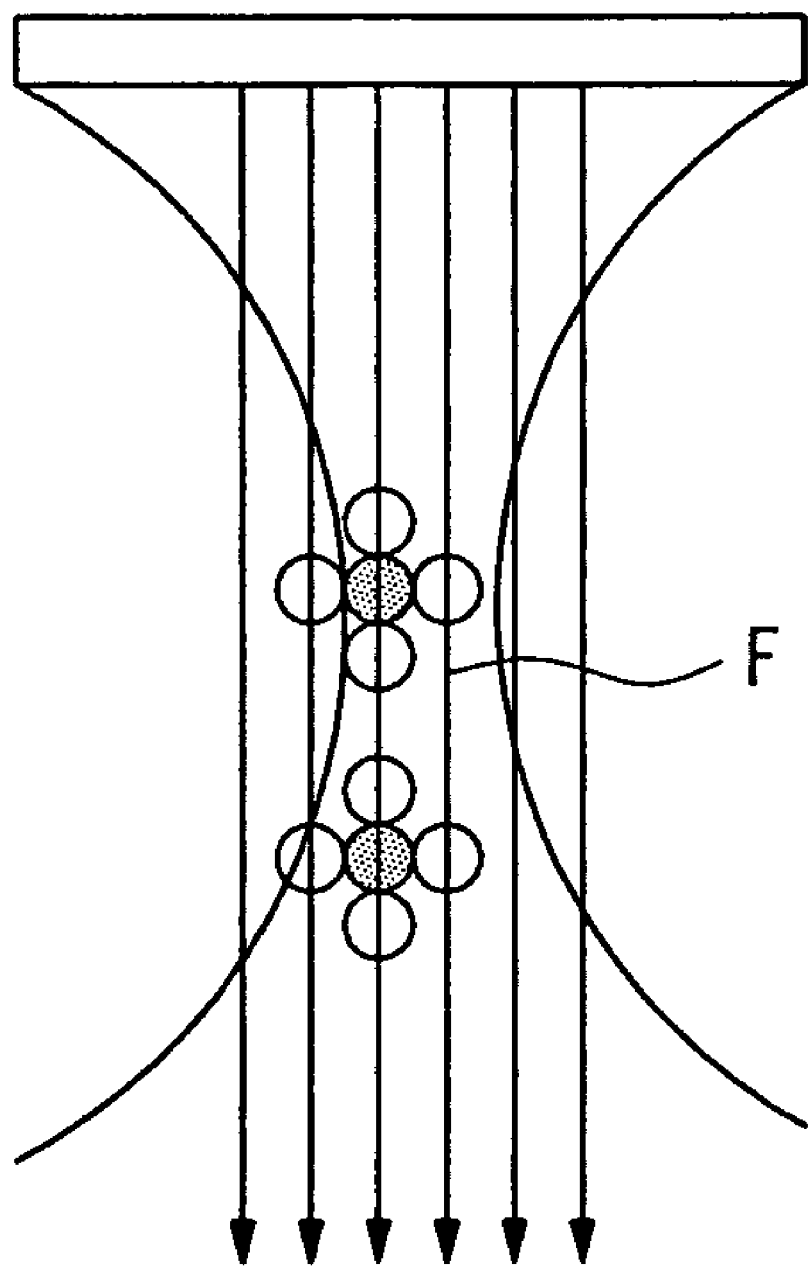
FIG. 12 is a schematic diagram for explaining a function of controlling filter coefficients in accordance with a focal position of a transmission beam in the fifth embodiment.
Figure 13:
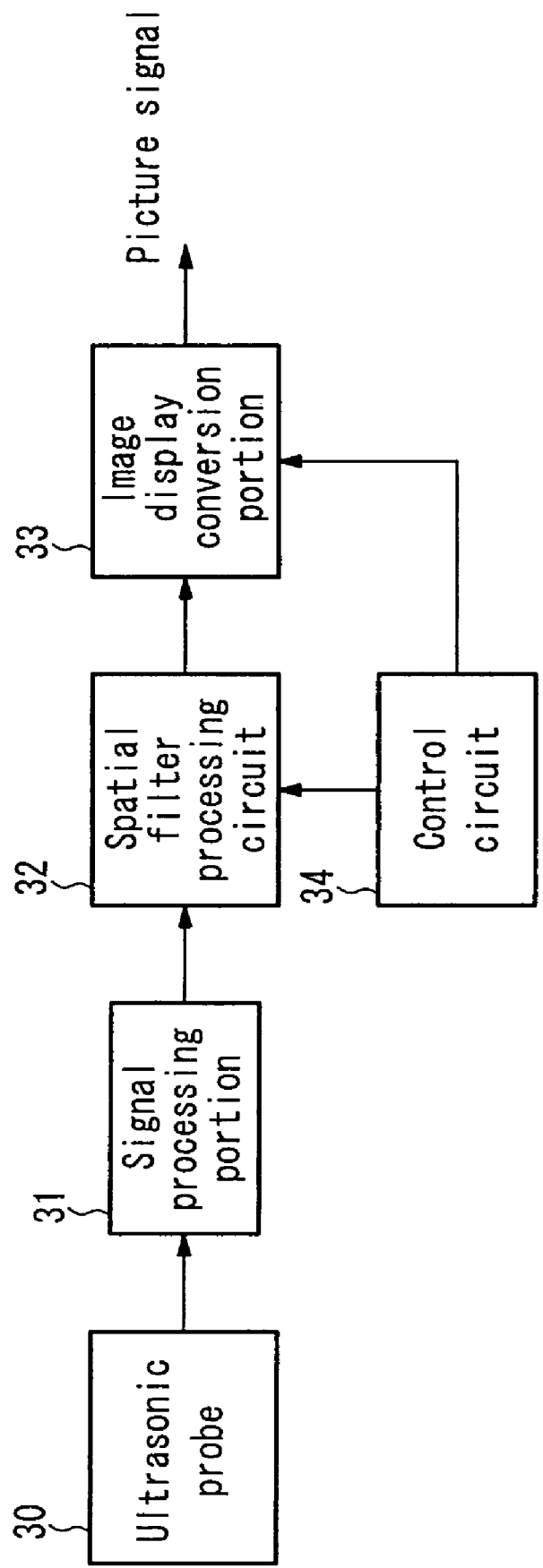
FIG. 13 is a functional block diagram showing an exemplary configuration of a conventional ultrasonic diagnosis apparatus.

With this configuration, it is possible to control filter coefficients in accordance with a focal position of a transmission beam. For example, in the case where a transmission beam is focused on a position F as shown in FIG. 12, filter coefficients of weak correlation are set for the vicinity of the focal position F of the transmission beam, and filter coefficients of strong correlation are set for positions away from the focal position F of the transmission beam. By optimizing the filter coefficients in this manner, it is possible to display a high-quality ultrasonic image that is uniform regardless of the focal position of the transmission beam.

INDUSTRIAL APPLICABILITY

The ultrasonic diagnosis apparatus according to the present invention is useful for displaying a high-quality ultrasonic image that is well defined in detail with reduced noticeable stripes seen in two-dimensional Doppler in a direction in which acoustic lines are arranged, with respect to signals between a plurality of reception beams obtained from a single transmission beam.

The invention claimed is:

1. An ultrasonic diagnosis apparatus, comprising:
a first storage unit configured to store digital reception beam data converted from a reception beam formed from an ultrasonic received signal;
a first control configured to control reading and writing of data from/in the first storage unit;
a filter coefficient calculation unit configured to calculate a filter coefficient based on information on the reception beam, the information including a positional relationship between the reception beam and a transmission beam;
a first spatial filter operation unit configured to subject each of a plurality of the reception beam data, including reception beam data converted from parallel reception beams received in parallel from a single transmission beam, to filtering for reducing a difference in image quality between adjacent beams based on the filter coefficient, thereby outputting image data; and
a scanning conversion unit configured to perform a scan conversion on the image data output from the first spatial filter operation unit so as to display an image on the display monitor,
wherein the first spatial filter operation unit also is configured to filter the reception beam data converted from the reception beams including one target reception beam and the adjacent plural reception beams, thereby generating the image data at a specified sampling point on the target reception beam, and
the filter coefficient calculation unit also is configured to apply the filter coefficient to the reception beam datum converted from the parallel reception beam received in parallel with the target reception beam so as to be smaller than the filter coefficient applied to the reception beam data which is converted from the reception beam other than the parallel reception beam and is symmetrical in positional relationship to the reception beam data with respect to a center at a position of the target reception beam.

2. The ultrasonic diagnosis apparatus according to claim 1, further comprising:
an ultrasonic reception data processing unit;
a two-dimensional Doppler signal processing unit for subjecting reception beam data from the ultrasonic reception data processing unit to two-dimensional Doppler processing;
a second storage unit for storing two-dimensional Doppler data output from the two-dimensional Doppler signal processing unit;
a second control for controlling reading and writing of data from/in the second storage unit; and
a second spatial filter operation unit for subjecting each of a plurality of the received two-dimensional Doppler data including data of beams received in parallel from a single transmission beam to filtering for reducing a difference in image quality between adjacent beams based on the filter coefficient supplied from the filter coefficient calculation unit.

3. The ultrasonic diagnosis apparatus according to claim 1, wherein the filter coefficient calculation unit is configured to control the filter coefficient in accordance with a receiving depth.

4. The ultrasonic diagnosis apparatus according to claim 1, wherein the filter coefficient calculation unit is configured to control the filter coefficient in accordance with an angle of the reception beam.

5. The ultrasonic diagnosis apparatus according to claim 1, wherein the filter coefficient calculation unit is configured to control the filter coefficient in accordance with a focal position of the transmission beam.

6. The ultrasonic diagnosis apparatus according to claim 1, further comprising:
a two-dimensional Doppler signal processing unit for subjecting reception beam data to two-dimensional Doppler processing;
a second storage unit for storing two-dimensional Doppler data output from the two-dimensional Doppler signal processing unit;
a second control for controlling reading and writing of data from/in the second storage unit; and
a second spatial filter operation unit for subjecting each of a plurality of the received two-dimensional Doppler data including data of beams received in parallel from a single transmission beam to filtering for reducing a difference in image quality between adjacent beams based on the filter coefficient supplied from the filter coefficient calculation unit.

* * * * *